(12) United States Patent
Rozman et al.

(10) Patent No.: US 9,867,853 B2
(45) Date of Patent: Jan. 16, 2018

(54) METHOD OF PROVIDING CELLULAR BASED IMMUNE ENHANCEMENT FOR RESTORING IMMUNITY AND PREVENTING AGE RELATED DISEASES

(71) Applicant: International Cell Technologies, Inc., Tucson, AZ (US)

(72) Inventors: Primoz Rozman, Ljubljana (SI); Thomas Bart, Basil (CH)

(73) Assignee: International Cell Technologies Inc., Tucson, AZ (US)

( * ) Notice: Subject to any disclaimer, the term of this patent is extended or adjusted under 35 U.S.C. 154(b) by 60 days.

(21) Appl. No.: 14/726,495

(22) Filed: May 30, 2015

(65) Prior Publication Data
US 2015/0342996 A1 Dec. 3, 2015

Related U.S. Application Data

(60) Provisional application No. 62/005,914, filed on May 30, 2014.

(51) Int. Cl.
| | |
|---|---|
| *A61K 48/00* | (2006.01) |
| *A61K 35/28* | (2015.01) |
| *A61K 35/12* | (2015.01) |

(52) U.S. Cl.
CPC ........ *A61K 35/28* (2013.01); *A61K 2035/124* (2013.01)

(58) Field of Classification Search
CPC .......................... A61K 25/38; A61K 2035/124
See application file for complete search history.

(56) References Cited

U.S. PATENT DOCUMENTS

| | | |
|---|---|---|
| 8,192,732 B2 | 6/2012 | Sugaya et al. |
| 2004/0151706 A1 | 8/2004 | Shakov et al. |
| 2004/0258673 A1 | 12/2004 | Hirose et al. |
| 2005/0276792 A1 | 12/2005 | Kaminski et al. |
| 2006/0233768 A1 | 10/2006 | Hirose et al. |
| 2007/0166289 A1 | 7/2007 | Hathaway et al. |
| 2008/0025953 A1 | 1/2008 | Sugaya et al. |
| 2008/0038231 A1 | 2/2008 | Rodgerson et al. |
| 2012/0123795 A1 | 5/2012 | Brevnova et al. |
| 2013/0052169 A1 | 2/2013 | Marom |
| 2014/0105871 A1 | 4/2014 | Turgeman et al. |
| 2017/0080031 A1* | 3/2017 | Li ........................ A61M 1/38 |

FOREIGN PATENT DOCUMENTS

WO 2015006474 1/2015

OTHER PUBLICATIONS

Pamphilon and Mijovic. Asian Journal of Transfusion Science 1(2):71-76, 2007. Printout pp. 1-10.*
Hovatta et al. Stem Cell Translational Medicine 3:1269-1274, 2014.*
Alonso-Fernandez P, De la Fuente M (2011) Role of the immune system in aging and longevity. Curr. Aging Sci. 4, 78-100.
Alonso-Fernandez P, Puerto M, Mate I, Ribera JM, De la Fuente M (2008) Neutrophils of centenarians show function levels similar to those of young adults. J Am Geriatr. Soc. 56, 2244-2251.
Arranz L, Fernandez C, Rodriguez A, Ribera JM, De la Fuente M (2008) The glutathione precursor N-acetylcysteine improves immune function in postmenopausal women. Free radical biology & medicine 45, 1252-1262.
Baron F, Maris MB, Storer BE, Sandmaier BM, Panse JP, Chauncey TR, Sorror M, Little MT, Maloney DG, Storb R, Heimfeld S (2005) High doses of transplanted CD34+ cells are associated with rapid T-cell engraftment and lessened risk of graft rejection, but not more graft-versus-host disease after nonmyeloablative conditioning and unrelated hematopoietic cell transplantation. Leukemia 19, 822-828.
Baruch K, Ron-Harel N, Gal H, Deczkowska A, Shifrut E, Ndifon W, Mirlas- Neisberg N, Cardon M, Vaknin 1, Cahalon L, Berkutzki T, Mattson MP, Gomez-Pinilla F, Friedman N, Schwartz M (2013) CNS-specific immunity at the choroid plexus shifts toward destructive Th2 inflammation in brain aging. Proc.Natl.Acad.Sci.U.S.A 110, 2264-2269.

(Continued)

*Primary Examiner* — Marcia S Noble

(57) ABSTRACT

A new and useful method is provided, for enhancing the immune system of a donor/recipient. Stem cells are collected from the donor/recipient at a time that the donor/recipient appears to have a healthy immune system, taking into consideration the age of the donor/recipient and the characteristics of a healthy immune system for a donor/recipient of that age. The stem cells are processed and stored in a condition that enables the stem cells to be later administered to that donor/recipient in predetermined amounts, in serial (consecutive) fashion, over predetermined time intervals, and at the later request of the donor/recipient, the stem cells are administered to the donor/recipient in serial (consecutive) fashion, over predetermined time intervals, to enhance the donor/recipient's immune system thereby preventing formation of age related diseases that are caused by rundown immune system. The practice of the present invention results in replenishing the hematopoietic system and primarily rebuilding the immune system in an aged individual. Also noteworthy, it refreshes the repertoire of stem cells, which are at the point of exhaustion, bringing about extension of life span and can also be used for improvement of cognitive functions of the donor/recipient.

16 Claims, 6 Drawing Sheets

(56) References Cited

OTHER PUBLICATIONS

Figure 1:
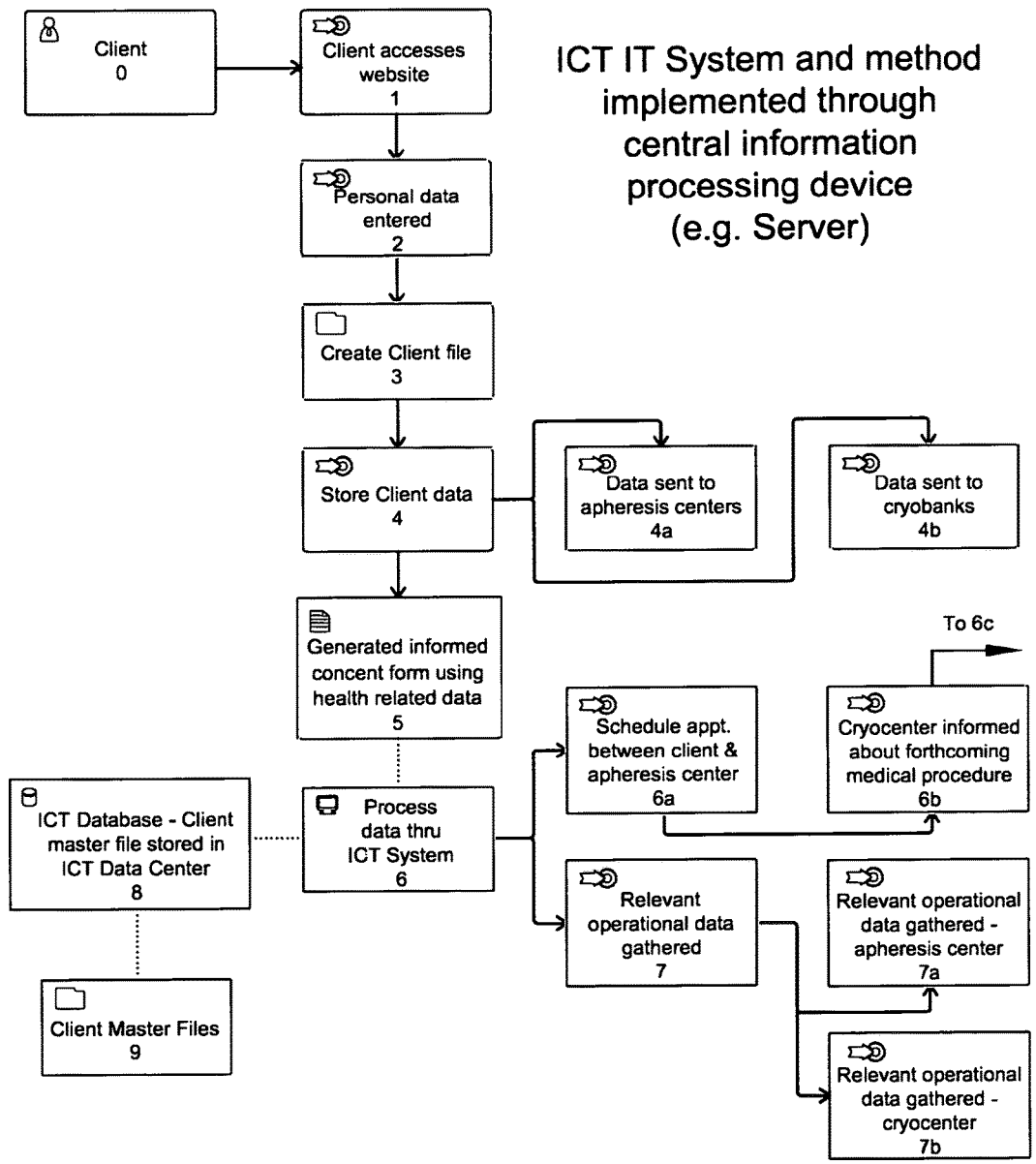

Baumgartner WA, Makinodan T, Bland WH (1980) In vivo evaluation of age-associated changes in delayed-type hypersensitivity. Mechanisms of ageing and development 12, 261-268.
Becker AJ, McCulloch EA, Till JE (1963) Cytological demonstration of the clonal nature of spleen colonies derived from transplanted mouse marrow cells. Nature 197, 452-454.
Bianconi E, Piovesan A, Facchin F, Beraudi A, Casadei R, Frabetti F, Vitale L, Pelleri MC, Tassani S, Piva F, Perez-Amodio S, Strippoli P, Canaider S (2013) An estimation of the number of cells in the human body. Ann.Hum.Biol. 40, 463-471.
Blomberg M, Rao S, Reilly J, Tiarks C, Peters S, Kittler E, Quesenberry P (1998) Repetitive bone marrow transplantation in nonmyeloablated recipients. Exp.Hematol. 26, 320-324.
Brecher G, Ansell JD, Micklem HS, Tjio JH, Cronkite EP (1982) Special proliferative sites are not needed for seeding and proliferation of transfused bone marrow cells in normal syngeneic mice. Proc.Natl.Acad.Sci.U.S.A 79, 5085-5087.
Brecher G, Tjio JH, Haley JE, Narla J, Beal SL (1979) Transplantation of murine bone marrow without prior host irradiation. Blood Cells 5, 237-246.
Broxmeyer, H.E. Will iPS Cells Enhance Therapeutic Applicability of Cord Blood Cells and Banking? Cell Stem Cell 2010; 6(l):21-24.
Butcher SK, Chahal H, Nayak L, Sinclair A, Henriquez NV, Sapey E, O'Mahony D, Lord JM (2001) Senescence in innate immune responses: reduced neutrophil phagocytic capacity and CD 16 expression in elderly humans. Journal of leukocyte biology 70, 881-886.
Colvin GA, Lambert JF, Abedi M, Hsieh CC, Carlson JE, Stewart FM, Quesenberry PJ (2004) Murine marrow cellularity and the concept of stem cell competition: geographic and quantitative determinants in stem cell biology. Leukemia 18, 575-583.
Conboy IM, Conboy MJ, Wagers AJ, Girma ER, Weissman IL, Rando TA (2005) Rejuvenation of aged progenitor cells by exposure to a young systemic environment. Nature 433, 760-764.
Conboy MJ, Conboy 1M, Rando TA (2013) Heterochronic parabiosis: historical perspective and methodological considerations for studies of aging and longevity. Aging Cell 12, 525-530.
Confer DL, Shaw BE, Pamphilon DH (2011) WMDA guidelines for subsequent donations following initial BM or PBSCs. Bone Marrow Transplant. 46, 1409-1412.
De le Fuente M (2008) Role of neuroimmunomodulation in aging. Neuroimmunomodulation 15, 213-223.
De la Fuente M, Hernanz A, Guayerbas N, Alvarez P, Alvarado C (2004) Changes with age in peritoneal macrophage functions. Implication of leukocytes in the oxidative stress of senescence. Cell Mol Biol 50 Online Pub, OL683-OL690.
De la Fuente M, Hernanz A, Vallejo MC (2005) The immune system in the oxidative stress conditions of aging and hypertension: favorable effects of antioxidants and physical exercise. Antioxid.Redox. Signal 7, 1356-1366.
De le Fuente M, Hernanz A, Guayerbas N, Victor VM, Arnalich F (2008) Vitamin E ingestion improves several immune functions in elderly men and women. Free radical research 42, 272-280.
Domen J, Wagers AJ, Weissman 1L (2006). Bone Marrow (Hematopoietic) Stem Cells. in: Regenerative Medicine, 2006. stemcells.nih/gov/info/scireport/pages/chapter5.aspx.
Egger G, Aigner R, Glasner A, Hofer HP, Mitterhammer H, Zelzer S (2004) Blood polymorphonuclear leukocyte migration as a predictive marker for infections in severe trauma: comparison with various inflammation parameters. Intensive care medicine 30, 331-334.
Fortin CF, Lesur O, Fulop T (2007) Effects of aging on triggering receptor expressed on myeloid cells (TREM)-I-induced PMN functions. FEBS letters 581, 1 173-1178.
Franceschi C, Cossarizza A (1995) Introduction: the reshaping of the immune system with age. International reviews of immunology 12, 1-4.
Franceschi C, Monti D, Sansoni P, Cossarizza A (1995) The immunology of exceptional individuals: the lesson of centenarians. Immunology today 16, 12-16.
Frasca D, Blomberg BB (2009) Effects of aging on B cell function. Current opinion in immunology 21, 425-430.
Frasca D, Landin AM, Lechner SC, Ryan JG, Schwartz R, Riley RL, Blomberg BB (2008) Aging down-regulates the transcription factor E2A, activation-induced cytidine deaminase, and Ig class switch in human B cells. Journal of immunology 180, 5283-5290.
Frasca D, Riley RL, Blomberg BB (2007) Aging murine B cells have decreased class switch induced by anti-CD40 or BAFF. Experimental gerontology 42, 192-203.
Gorin NC, Labopin M, Boiron JM, Theorin N, Littlewood T, Slavin S, Greinix H, Cahn JY, Alessandrino EP, Rambaldi A, Nagler A, Polge E, Rocha V (2006) Results of genoidentical hemopoietic stem cell transplantation with reduced intensity conditioning for acute myelocytic leukemia: higher doses of stem cells infused benefit patients receiving transplants in second remission or beyond—the Acute Leukemia Working Party of the European Cooperative Group for Blood and Marrow Transplantation. J.Clin.Oncol. 24, 3959-3966.
Goronzy JJ, Zettl A, Weyand CM (1998) T cell receptor repertoire in rheumatoid arthritis. International reviews of immunology 17, 339-363.
Hauge AW, Haastrup EK, Sengelov H, Minulescu L, Dickmeiss E, Fischer-Nielsen A (2014) Addition of plerixafor for CD34+ cell mobilization in six healthy stem cell donors ensured satisfactory grafts for transplantation. Transfusion 54, 1055-1058.
Holstege H. Pfeiffer W, Sie D, Hulsman M, Nicholas TJ, Lee CC, Ross T, Lin J, Miller MA, Ylstra B, Meijers-Heijboer H, Brugman MH, Staal FJ, Holstege G, Reinders MJ, Harkins TT, Levy S, Sistermans EA (2014) Somatic mutations found in the healthy blood compartment of a 115-yr-old woman demonstrate oligoclonal hematopoiesis. Genome Res. 24, 733-742.
Jiang L, Malik S, Litzow M, Gastineau D, Micallef I, Roy V, Solberg L, Zubair AC (2012) Hematopoietic stem cells from poor and good mobilizers are qualitatively equivalent. Transfusion 52, 542-548.
Katsimpardi L, Litterman NK, Schein PA, Miller CM, Loffredo FS, Wojtkiewicz GR, Chen JW, Lee RT, Wagers AJ, Rubin LL (2014) Vascular and Neurogenic Rejuvenation of the Aging Mouse Brain by Young Systemic Factors. Science.
Keating GM (2011) Plerixafor: a review of its use in stem-cell mobilization in patients with lymphoma or multiple myeloma. Drugs 71, 1623-1647.
Kowald A & Kirkwood TB 2014. Transcription could be the key to the selection advantage of mitochondrial deletion mutants in aging. Proc Natl Acad Sci U S A, 111, 2972-7.
Kovina MV, Zuev VA, Kagarlitskiy GO, Khodarovich YM (2013) Effect on lifespan of high yield non-myeloablating transplantation of bone marrow from young to old mice. Front Genet. 4, 144.
Lavasani M, Robinson AR, Lu A, Song M, Feduska JM, Ahani B, Tilstra JS, Feldman CH, Robbins PD, Niedemhofer LJ, Huard J (2012) Muscle-derived stem/progenitor cell dysfunction limits healthspan and lifespan in a murine progeria model. Nature communications 3, 608.
Lazuardi L, Jenewein B, Wolf AM, Pfister G, Tzankov A, Grubeck-Loebenstein B (2005) Age-related loss of naive T cells and dysregulation of T-cell/B-cell interactions in human lymph nodes. Immunology 114, 37-43.
Linton PJ, Dorshkind K (2004) Age-related changes in lymphocyte development and function, Nat.Immunol. 5, 133-139.
Listi F, Candore G, Modica MA, Russo M, Di Lorenzo G, Esposito-Pellitteri M, Colonna-Romano G, Aquino A, Bulati M, Lio D, Franceschi C, Caruso C (2006) A study of serum immunoglobulin levels in elderly persons that provides new insights into B cell immunosenescence. Annals of the New York Academy of Sciences 1089, 487-495.
Loffredo FS, Steinhauser ML, Jay SM, Gannon J, Pancoast JR, Yalamanchi P, Sinha M, Dall'Osso C, Khong D, Shadrach JL, Miller CM, Singer BS, Stewart A, Psychogios N, Gerszten RE, Hartigan AJ, Kim MJ, Serwold T, Wagers AJ, Lee RT (2013) Growth differentiation factor 11 is a circulating factor that reverses age-related cardiac hypertrophy. Cell 153, 828-839.

(56) References Cited

OTHER PUBLICATIONS

Loison A, Festa-Bianchet M, Gaillard JM, Jorgenson JT, Jullien JM (1999) Age-specific survival in five populations of ungulates: Evidence of senescence. Ecology 80, 2539-2554.
Lord JM, Butcher S, Killampali V, Lascelles D, Salmon M (2001) Neutrophil ageing and immunesenescence. Mechanisms of ageing and development 122, 1521-1535.
Manz RA, Thiel A, Radbruch A (1997) Lifetime of plasma cells in the bone marrow. Nature 388, 133-134.
Mazur, P. (1970) Cryobiology: the freezing of biological systems. Science (New York, N.Y.) vol. 168:939-949.
Micklem HS, Clarke CM, Evans EP, Ford CE (1968) Fate of chromosome-marked mouse bone marrow cells tranfused into normal syngeneic recipients. Transplantation 6, 299-302.
Miller RA (1996) The aging immune system: primer and prospectus. Science 273, 70-74.
Naylor K, Li G, Vallejo AN, Lee WW, Koetz K, Bryl E, Witkowski J, Fulbright J, Weyand CM, Goronzy JJ (2005) The influence of age on T cell generation and TCR diversity. Journal of immunology 174, 7446-7452.
Nietfeld JJ, Pasquini MC, Logan BR, Verter F, Horowitz MM (2008). Lifetime probabilities of hematopoietic stem cell transplantation in the U.S. Biol Blood Marrow Transplant. Mar;14(3):316-22.
Nilsson SK, Dooner MS, Weier HU, Frenkel B, Lian JB, Stein GS, Quesenberry PJ (1999) Cells capable of bone production engraft from whole bone marrow transplants in nonablated mice. J.Exp. Med. 189, 729-734.
Niwa Y, Kasama T, Miyachi Y, Kanoh T (1989) Neutrophil chemotaxis, phagocytosis and parameters of reactive oxygen species in human aging: cross-sectional and longitudinal studies. Life sciences 44, 1655-1664.
Njemini R, Lambert M, Demanet C, Mets T (2005) Heat shock protein 32 in human peripheral blood mononuclear cells: effect of aging and inflammation. Journal of clinical immunology 25, 405-417.
Ortega E, Garcia JJ, De la Fuente M (2000) Ageing modulates some aspects of the non-specific immune response of murine macrophages and lymphocytes. Exp Physiol 85,519-525.
Plett PA, Frankovitz SM, Orschell-Traycoff CM (2002) In vivo trafficking, cell cycle activity, and engraftment potential of phenotypically defined primitive hematopoietic cells after transplantation into irradiated or nonirradiated recipients. Blood 100, 3545-3552.
Pulsipher MA, Chitphakdithai P, Logan BR, Leitman SF, Anderlini P, Klein JP, Horowitz MM, Miller JP, King RJ, Confer DL (2009) Donor, recipient, and transplant characteristics as risk factors after unrelated donor PBSC transplantation: beneficial effects of higher CD34+ cell dose. Blood 114, 2606-2616.
Quesenberry PJ, Ramshaw H, Crittenden RB, Stewart FM, Rao S, Peters S, Becker P, Lowry P, Blomberg M, Reilly J,. (1994) Engraftment of normal murine marrow into nonmyeloablated host mice. Blood Cells 20, 348-350.
Quesenberry PJ, Stewart MF, Peters S, Nillson S, Ramshaw H, Rao S, Tiarks C, Zhong S, Frimberger A, Reilly J (1997) Engraftment of hematopoietic stem cells in nonmyeloablated and myeloablated hosts. Stem Cells 15 Suppl 1, 167-169.
Raffoux C, Gluckman E (1993) Suggested strategies for establishing an HLA-typed cord blood bank. Journal of hematotherapy 2, 263-264.
Ramshaw HS, Crittenden RB, Dooner M, Peters SO, Rao SS, Quesenberry PJ (1995a) High levels of engraftment with a single infusion of bone marrow cells into normal unprepared mice. Biol. Blood Marrow Transplant. 1, 74-80.
Ramshaw HS, Rao SS, Crittenden RB, Peters SO, Weier HU, Quesenberry PJ (1995b) Engraftment of bone marrow cells into normal unprepared hosts: effects of 5-fluorouracil and cell cycle status. Blood 86, 924-929.
Rao SS, Peters SO, Crittenden RB, Stewart FM, Ramshaw HS, Quesenberry PJ (1997) Stem cell transplantation in the normal nonmyeloablated host: relationship between cell dose, schedule, and engraftment. Exp.Hematol. 25, 114-121.

Ratajczak MZ, Shin DM, Liu R, Mierzejewska K, Ratajczak J, Kucia M, Zuba-Surma EK (2012) Very small embryonic/epiblast-like stem cells (VSELs) and their potential role in aging and organ rejuvenation—an update and comparison to other primitive small stem cells isolated from adult tissues. Aging 4, 235-246.
Ratajczak MZ, Zuba-Surma EK, Shin DM, Ratajczak J, Kucia M (2008) Very small embryonic-like (VSEL) stem cells in adult organs and their potential role in rejuvenation of tissues and longevity. Exp.Gerontol. 43, 1009-1017.
Ruckh JM, Zhao JW, Shadrach JL, van WP, Rao TN, Wagers AJ, Franklin RJ (2012) Rejuvenation of regeneration in the aging central nervous system. Cell Stem Cell 10, 96-103.
Saxe DF, Boggs SS, Boggs DR (1984) Transplantation of chromosomally marked syngeneic marrow cells into mice not subjected to hematopoietic stem cell depletion. Exp.Hematol. 12, 277-283.
Sebastian C, Espia M, Serra M, Celada A, loberas J (2005) MacrophAging: a cellular and molecular review. Immunobiology 210, 121-126.
Shen J, Tsai YT, Dimarco NM, Long MA, Sun X, Tang L (2011) Transplantation of mesenchymal stem cells from young donors delays aging in mice. Sci.Rep. 1, 67.
Shi Y, Yamazaki T, Okubo Y, Uehara Y, Sugane K, Agematsu K (2005) Regulation of aged humoral immune defense against pneumococcal bacteria by IgM memory B cell. Journal of immunology 175, 3262-3267.
Solana R, Pawelec G, Tarazona R (2006) Aging and innate immunity. Immunity 24, 491-494.
Sonnega, A. The Future of Human Life Expectancy: Have We Reached the Ceiling or is the Sky the Limit? Research Highlights in the Demography and Economics of Aging No. 8 Mar. 2006.
Spurr EE, Wiggins NE, Marsden KA, Lowenthal RM, Ragg SJ (2002) Cryopreserved human haematopoietic stem cells retain engraftment potential after extended (5-14 years) cryostorage. Cryobiology 44, 210-217.
Stephan RP, Sanders VM, Witte PL (1996) Stage-specific alterations in murine B lymphopoiesis with age. International immunology 8, 509-518.
Stewart FM, Crittenden RB, Lowry PA, Pearson-White S, Quesenberry PJ (1993a) Long-term engraftment of normal and post-5-fluorouracil murine marrow into normal nonmyeloablated mice. Blood 81, 2566-2571.
Stewart FM, Temeles D, Lowry P, Thraves T, Grosh WW, Quesenberry PJ (1993b) Post-5-fluorouracil human marrow: stem cell characteristics and renewal properties after autologous marrow transplantation. Blood 81, 2283-2289.
Till JE, McCulloch EA (1961) A direct measurement of the radiation sensitivity of normal mouse bone marrow cells. Radiat.Res. 14, 213-222. ri.
To LB, Levesque JP, Herbert KE (2011) How I treat patients who mobilize hematopoietic stem cells poorly. Blood 118, 4530-4540.
Tortorella C, Simone O, Piazzolla G, Stella I, Antonaci S (2007) Age-related impairment of GM-CSF-induced signalling in neutrophils: role of SHP-1 and SOCS proteins. Ageing research reviews 6, 81-93.
van Praag H., Shubert T, Zhao C, Gage FH (2005) Exercise enhances learning and hippocampal neurogenesis in aged mice. J.Neurosci. 25, 8680-8685.
Villeda SA, Luo J, Mosher KI, Zou B, Britschgi M, Bieri G, Stan TM, Fainberg N, Ding Z, Eggel A, Lucin KM, Czirr E, Park JS, Couillard-Despres S, Aigner L, Li G, Peskind ER, Kaye JA, Quinn JF, Galasko DR, Xie XS, Rando TA, Wyss-Corey T (2011) The ageing systemic milleu negatively regulates neurogenesis and cognitive function. Nature 477, 90-94.
Villeda SA, Plambeck KE, Middeldorp J, Castellano JM, Mosher KI, Luo J, Smith LK, Bieri G, Lin K, Berdnik D, Wabl R, Udeochu J, Wheatley EG, Zou B, Simmons DA, Xie XS, Longo FM, Wyss-Coray T (2014) Young blood reverses age-related impairments in cognitive function and synaptic plasticity in mice. Nat. Med. 20(6): 659-663.

(56) References Cited

OTHER PUBLICATIONS

Weinberger B, Herndler-Brandstetter D, Schwanninger A, Weiskopf D, Grubeck-Loebenstein B (2008) Biology of immune responses to vaccines in elderly persons. Clinical infectious diseases 46, 1078-1084.

Weksler ME (2000) Changes in the B-cell repertoire with age. Vaccine 18, 1624-1628.

Weksler ME, Szabo P (2000) The effect of age on the B-cell repertoire. Journal of clinical immunology 20, 240-249.

Wenisch C, Patruta S, Daxbock F, Krause R, Plorl W (2000) Effect of age on human neutrophil function. Journal of leukocyte biology 67, 40-45.

Wu DD, Keating A (1993) Hematopoietic stem cells engraft in untreated transplant recipients. Exp.Hematol. 21,251-256.

Yu BP, Chung HY (2001) Oxidative stress and vascular aging. Diabetes research and clinical practice 54 Suppl 2, S73-S80.

Zheng S, Han S, Takahashi Y, Kelsoe G (1997) Immunosenescence and germinal center reaction. Immunological reviews 160, 63-77.

Zuba-Surma EK, Wu W, Ratajczak J, Kucia M, Ratajczak MZ (2009) Very small embryonic-like stem cells in adult tissues-potential implications for aging. Mech.Ageing Dev. 130,58-66.

Blurton-Jones et al. "Neural stem cells improve. cognition via BDNF in a transgenic model of Alzheimer disease" Proc Natl Acad Sci USA. 2009, 106: 13594-13599.

Lunn et al. "Stem Cell Technology for Neurodegenerative Diseases" Ann Neurol. Sep. 2011; 70(3): 353-361.

Purandare et al. "Therapeutic potential of autologous stem cell transplantation for cerebral palsy" Case Rep Transplant. Epub Oct. 4, 2012.

\* cited by examiner

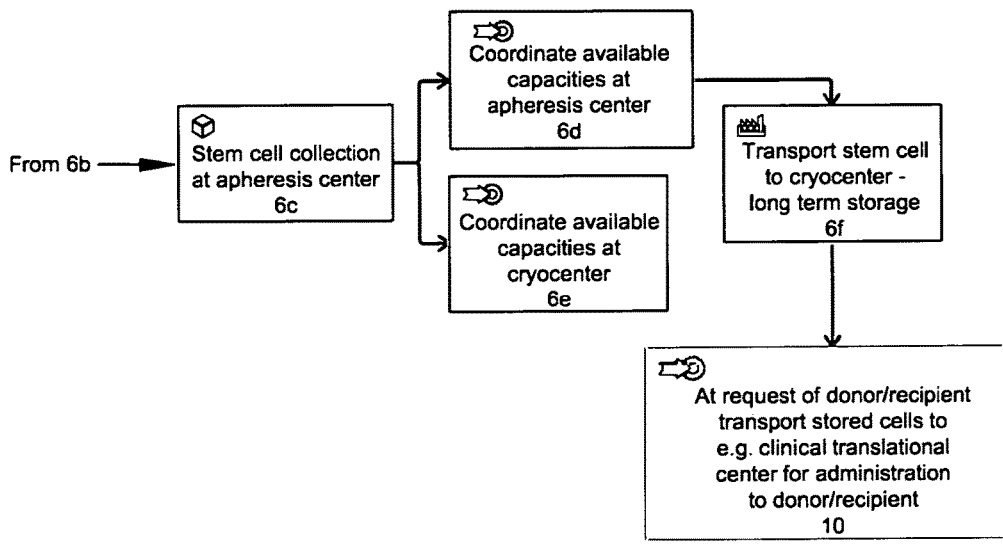
FIG. 1 (continued)
Legend
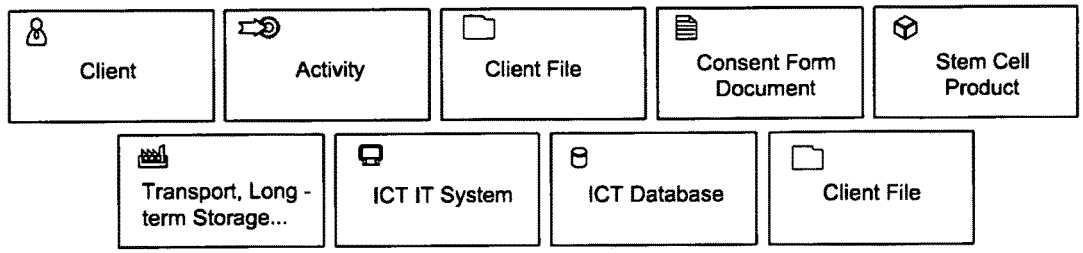

Legend: The highest rate of engraftment into host BM achieved in animal experiments was around 56%, which shows that displacement of host aged stem cells can not be complete in non-myeloablative setting.

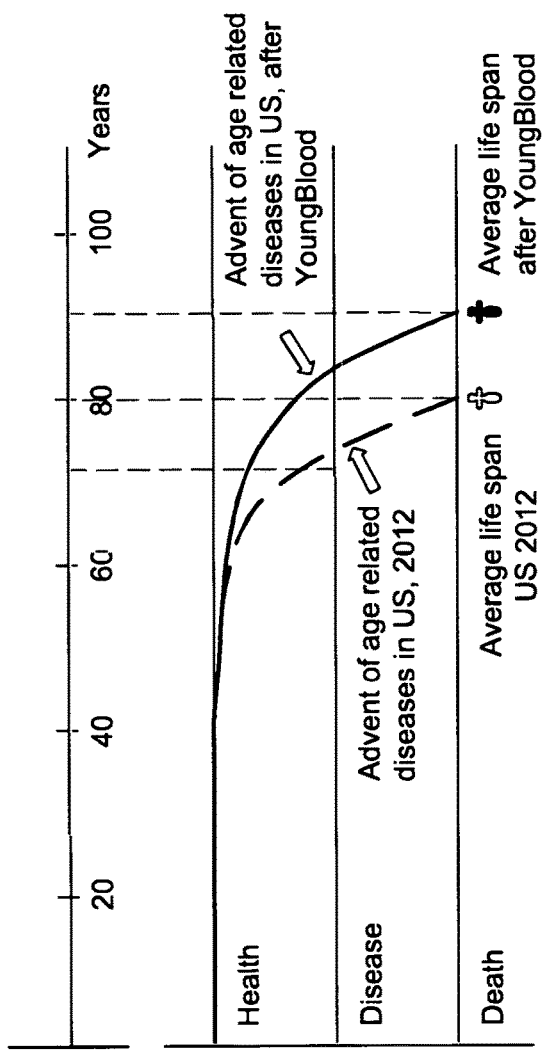

FIG. 3

Legend: The life expectancy at birth of US citizen in 2012 was 79 years (76 for men and 81 for women), whereas the healthy life expectancy at birth (HALE) - i.e. the average number of years that a person can expect to live "full health" - was 70 years. Therefore the optimal age for starting prevention with the YoungBlood™ immune enhancement product is before 70 years of age, (e.g. between 50 - 70 years of age), if the person is generally healthy. This will increase the period of full health at least until 80 years of age, postpone the appearance of disease and increase the life span accordingly.

FIG. 4

FIG 4. Calculation of HSC numbers in mice and humans and percentage of obtained chimerism in the bone marrow. Linear approximation.$

| Nr. of BM TNCs transplanted – mouse study | % chimerism (if 1M cells results in 0.17% chimerism) Colvin 2004. Ramshaw 1995 | % chimerism (if 1M cells results in 0.28% chimerism Rao 1997 | Calculated chimerism in man (average) | Nr. of human TNCs (mouse x 3500 in 70kg) | Necessary nr. of human CD34+ HSCs (if frequency 1 in 10.000 TNCs) |
|---|---|---|---|---|---|
| 1 x 10(6) | 0.17% | 0.28% | 0.23% | 3.5 x 10(9) | 0.35 x 10(6) |
| 10 x 10(6) | 1.7 % | 2.8 % | 2.3 % | 35 x 10(9) | 3.5 x 10(6) |
| 40 x 10(6) | 6.8 % | 11.2 % | 9.0 % | 140x 10(9) | 14 x 10(6) |
| 60 x 10(6) | 10.2 % | 16.8 % | 13.5% | 210x 10(9) | 21 x 10(6) |
| 80 x 10(6) | 13.6 % | 22.4 % | 18.0% | 280x 10(9) | 28 x 10(6) |
| 100 x 10(6) | 17 % | 28 % | 22.5% | 350x 10(9) | 35 x 10(6) |
| 120 x 10(6) | 20.4 % | 33.6 % | 27.0% | 420x 10(9) | 42 x 10(6) |
| 160 x 10(6) | 27.2 % | 44.8 % | 36.0% | 560 x 10(9) | 56 x 10(6) |
| 180 x 10(6) | 30.6 % | 50.4 % | 40.5% | 630 x 10(9) | 63 x 10(6) |
| 200 x 10(6) | 34 % | 56 % | 45.0% | 700x 10(9) | 70 x 10(6) |
| 220 x 10(6) | 37.4 % | 61.6 % | 49.5 % | 770 x 10(9) | 77 x 10(6) |
| 240 x 10(6) | 40.8 % | 67.2 % | 54.0 % | 840 x 10(9) | 84 x 10(6) |
| 280 x 10(6) | 47.6 % | 78.4 % | 63.0 % | 980 x 10(9) | 98 x 10(6) |
| 300 x 10(6) | 51% | 84 % | 67.5 % | 1050 x 10(9) | 105 x 10(6) |
| 417 x 10(6) | 70.9% | 116% | 94% | 1400 x 10(9) | 140 x 10(6)* |
| 444 x 10(6) | 75.5% | 124.3% | 100% | 1500 x 10(9) | 150 x 10(6) |
| 500 x 10(6)** | 85% | 140% | 112.5% | 1700 x 10(9) | 170 x 10(6)*** |
| 797 x 10(6) | 135% | 223 % | 179.0 % | 2.789 x 10(9) | 279 x 10(6)# |

$ In the murine experiments, 800 x 10(6) cells was the maximal dose transplanted, and the increase of chimerism % had a decreasing tendency, usually not increasing 60% of chimerism.
* Theoretical lowest number of HSCs for autologous transplantation in 70 kg individual is 140 x 10(6)
** Theoretical number of all nucleated cells in BM of adult mouse is approx. 500 x 10(6)
*** Theoretical number of all nucleated cells in human BM is between 1,5-1,7 x 10(12), rendering a total number of 170 x 10(6) HSCs, if frequency of HSC is 1 in 10,000 BMCs (Colvin 2004, Kovina 2013, Bianconi 2013)
The actual average number of HSCs in one collected HSC unit from a mobilized healthy donor (BTC Ljubljana, 2011-2012).

Note: An adult female BALB-c mouse weights on average 20g and possesses approx. 500 -600 x 10 (6) bone marrow cells (Kovina et al. 2013; Colvin et al. 2004). Based on simple comparison, 70 kg human adult has around 1.7 x 10 (12) bone marrow cells. If more elaborated data of Bianconi 2013 is used, the total human cell number is 3.72 x 10 (13) and the bone marrow consisting of 4% of the total body mass contains approx. 1.5x10(12) cells (Bianconi et al. 2013).

FIG. 5

FIG 5. Average figures of 1 mobilized product of HSC (26 apheresis procedures, healthy donors, collected in BTC Ljubljana 2012-13)

| Average volume | 197mL |
|---|---|
| Absolute nr. of all nucleated cells (TNC) in 1 unit | $39,3 \times 10(9)$; |
| Percent of MNCs | 66,3% of all TNCs |
| Absolute nr. of MNCs in 1 unit | $25,0 \times 10(9)$ |
| Average absolute CD34+ count in 1 unit | $279 \times 10(6)$ |

METHOD OF PROVIDING CELLULAR BASED IMMUNE ENHANCEMENT FOR RESTORING IMMUNITY AND PREVENTING AGE RELATED DISEASES

RELATED APPLICATION/CLAIM OF PRIORITY

This application is related to and claims priority from U.S. provisional application Ser. No. 62/005,904, filed May 30, 2014, which provisional application is incorporated by reference herein.

BACKGROUND

The present invention relates to a new and useful method of providing cellular based immune enhancement for restoring immunity and preventing age related diseases. In particular, the present invention provides a method for enhancing the immune system of a donor/recipient (i.e. a donor who desires to have his/her stem cells administered to that donor/recipient to enhance the donor/recipient's immune system), by collecting stem cells from the donor/recipient while the donor/recipient appears to have a healthy immune system, storing the stem cells (as a product sometimes referred to herein as the YoungBlood™ product), and later administering the stored product to that donor/recipient, in a manner that enhances the immune system of that donor/recipient. Enhancement pertains to replacement of old immune cell progenitors in the bone marrow with the young and fully competent cells.

The present invention provides a new and useful method that utilizes a donor/recipient's own stem cells at a time, or under circumstances, designed to enhance the donor/recipient's immune system and prolong the healthy life span of the donor/recipient.

Age related formation of reactive oxygen species (ROS) and chronic inflammation (oxi-inflamm-aging) and probably some other factors lead to impaired homeostasis of innate and acquired immune response in humans. The results of dysfunction of the immune system are malignant diseases, atherosclerosis and infections, which are the leading causes of death of elderly people. More than half of these illnesses are closely associated with the impaired immunity. (Alonso-Fernandez P, De la Fuente M (2011); De la Fuente M, Hernanz A, Vallejo MC (2005); Solana R, Pawelec G, Tarazona R (2006); Weinberger B, Herndler-Brandstetter D, Schwanninger A, et al. (2008), Kowald and Kirkwood (2014).

SUMMARY OF THE INVENTION

The present invention provides a new and useful method that utilizes a donor/recipient's own stem cells (collected and stored, as the YoungBlood™ product, when that donor/recipient is in a healthy state) to enhance the donor/recipient's immune system, and potentially prolong that donor/recipient's healthy life span. In this application reference to a "donor/recipient" means the person who donates the stem cells when that person appears to have a healthy immune system (preferably in his/her youth), and who also receives administration of the donated stem cells (i.e. the YoungBlood™ product) when that person's immune system can be enhanced, and the person's healthy life span can be increased. Also, as those in the art will also recognize, the administration of the YoungBlood™ product involves transfusion of the product to the donor/recipient (the mechanism by which the cells are delivered into the donor/recipient), and transplantation of the stem cells into the biological tissue of the donor/recipient (the process by which the stem cells displace older stem cells of the donor/recipient).

According to the invention the immune system of a donor/recipient is enhanced by (a) collecting stem cells from the donor/recipient at a time that the donor/recipient appears to have a healthy immune system, taking into consideration the age of the donor/recipient and the characteristics of a healthy immune system for a donor/recipient of that age, (b) processing the stem cells and storing the stem cells (as the YoungBlood™ product) in a condition that enables the stem cells to be later administered to that donor/recipient in predetermined amounts, in serial (consecutive) fashion, over predetermined time intervals, (c) at the later request of the donor/recipient, further administering the stem cells to the donor/recipient in serial (consecutive) fashion, over predetermined time intervals, to enhance the donor/recipient's immune system, and d) enhancement stands for partial displacement of old population of old and compromised immune reservoir in the bone marrow that can exhibit unwanted phenomena of aged and senescent immunity, resulting in age related immune deficiencies, and their supplementation with young, immune competent cells of the same individual.

By enhancing the donor/recipient's immune system in this preventive manner, the donor/recipient's healthy life span can be increased. The later request of the donor/recipient can be because the donor/recipient wants the administration to enhance his/her immune system, or when the donor/recipient, in consultation with medical personnel, agrees that administration of the stem cells is likely to enhance his/her immune system.

In several exemplary versions of the method of the present invention, the collection of stem cells from the donor/recipient includes dividing the final collected product (the YoungBlood™ product) into a plurality of aliquots, each of which includes a sufficient number of CD34+ stem cells such that when one or more aliquots is (are) administered to the donor/recipient, a predetermined, targeted chimerism can be expected in the bone marrow of the donor/recipient.

In implementing the present invention a central processing system (e.g. a server) is selectively placed (i) in circuit communication with the donor/recipient, to collect relevant data from the donor/recipient, (ii) in circuit communication with an apheresis center for collecting the stem cells, and (iii) in circuit communication with a processing and cell storing center for administering the storing of the cells (as part of the YoungBlood™ product) and delivering the product for administration to the patient. Generally the delivery of the product for administration will be accomplished at a later stage of the donor/recipient's expected life cycle, at a time or under circumstances that suggest the donor/recipient's immune system will be enhanced, and thereby his/her healthy life span may be increased. In a preferred implementation of the invention, the central processing system is selectively placed in circuit communication with the donor/recipient (referred to as the "client") via a website, and relevant data is collected from the donor/recipient. The relevant data includes donor/recipient data that includes administrative, financial, health (medical) related data. A client file for the donor/recipient is created by the central processing system, and all data collected from the donor/recipient is stored in the client file, under the control of the central processing system. An informed consent form is generated by the central processing system, using the health related data from the donor/recipient, and sent either to the donor/recipient, or to an apheresis center for initial review by appropriate medical personnel before being sent to the donor/recipient, and the informed consent form is then sent to the donor/recipient for execution by the donor/recipient (in this application "review" encompasses discussion, analysis, or any other means by which information can be sent to the donor/recipient for an informed consent). The relevant data collected from the donor/recipient that relates to the collection, storage and administration of the donor/recipient's stem cells is transmitted to one or more apheresis centers and cryocenter (according to the donor/recipient's wishes in timing and proximity), and an appointment between the donor/recipient and apheresis center is then made, and the cryocenter is informed about the forthcoming medical procedure (stem cell collection at apheresis center, processing of the collected cells to provide the Young-Blood™ product, and subsequent transport of the product to the cryocenter for long-term storage), and relevant operational data is provided to the apheresis center and the cryocenter.

All data will be available to the client (donor/recipient) in an e-banking fashion, with a personal account, control, etc.

There are various situations where the administration of the donor/recipient's stem cells (i.e. as the YoungBlood™ product) will be particularly beneficial to the donor/recipient. For example, the administration of the cells to the donor/recipient can be performed when the donor/recipient presents symptoms of impairment of the immune system. Alternatively the administration of the cells is performed when the donor/recipient shows impairment or fading of the donor/recipient's sexual function (i.e. impairment or fading of reproductive capacity and sexual functions, as would be understood by those in the art), because impairment of sexual function is often associated and paralleled with the aging of the donor/recipient and with impairment of the donor/recipient's immune system. Still another alternative is to administer the stem cells as a preventive measure to the donor/recipient in full health, but in the last quarter of the donor/recipient's life expectancy (or at a predetermined age, which is preferably around 50-70 yrs of age in US population), since that is often the time in which enhancing the immune system can be beneficial to increasing the donor/recipient's healthy life span.

In addition, there are aspects of the present invention that are useful in addressing other conditions that may not be directly linked to impairment of the donor/recipient's immune system. For example, administration of the applicants' product is useful in enhancing the cognitive function of a donor/recipient when administered at a time, or under circumstances, in which the donor/recipient's cognitive functions may be at risk (e.g. if the donor/recipient is at risk for Alzheimer's or age related dementia).

Other features of the present invention will become further apparent from the following detailed description and the accompanying drawing.

BRIEF DESCRIPTION OF THE DRAWINGS, TABLES AND EXHIBIT

Figure 2:
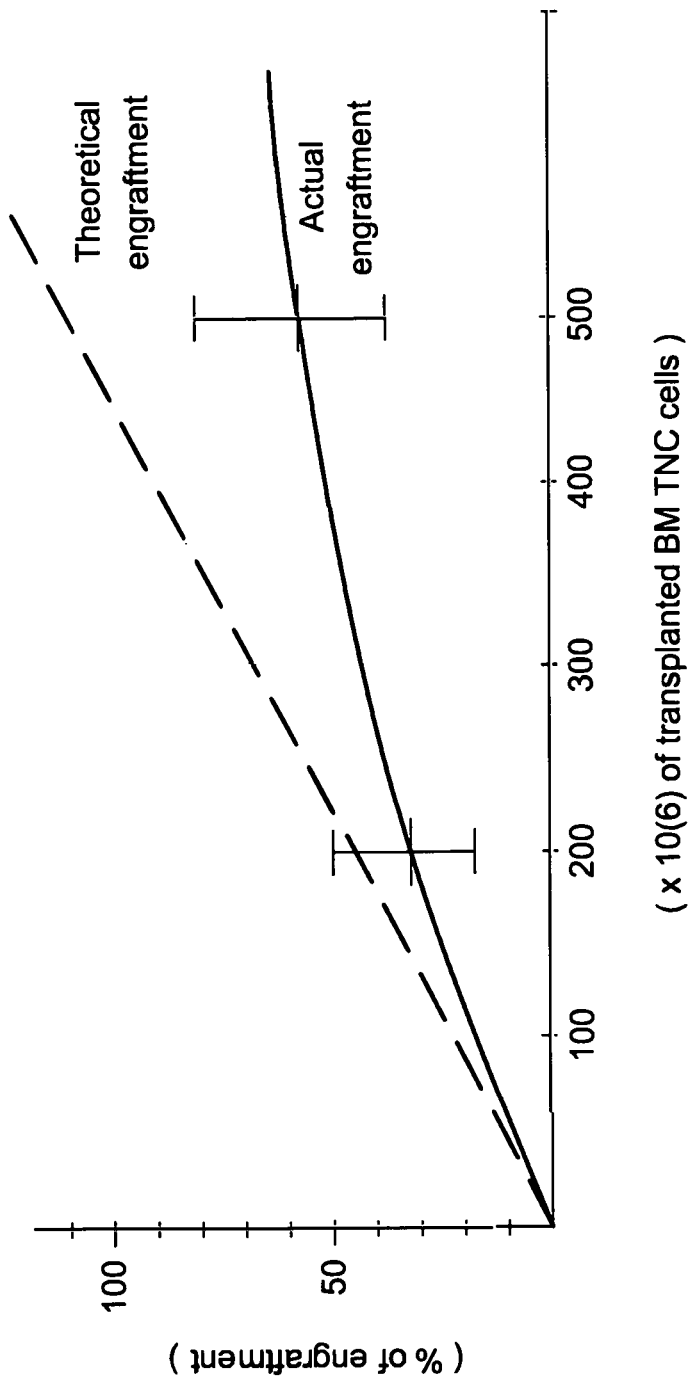

FIGS. 1a and 1b provide a schematic illustration of the system components and method by which the principles of the present invention are carried out;

FIG. 2 shows the rate of homing/displacement of stem cells, based on animal experimentation from several authors; and FIG. 3 schematically illustrates the applicant's expectation of the manner in which an extension of a donor/recipient's healthy life span might result from the practice of the present invention and based on current epidemiological data for US and worldwide.

Tables 1 and 2 are described herein

Exhibit A is a copy of FIG. 1 from provisional application Ser. No. 62/005,904.

DETAILED DESCRIPTION

As discussed above, the present invention relates to a new and useful method that utilizes a donor/recipient's own stem cells (collected when that donor/recipient is in a healthy condition) to enhance the donor/recipient's immune system, and by preventing development of usual age related diseases, potentially prolong that donor/recipient's healthy life span. The following description will describe the basis for applicants' concept of utilizing a donor/recipient's own stem cells (as the YoungBlood™ product) to enhance the donor/recipient's immune system, and potentially prolong that donor/recipient's healthy life span, as well as the applicant's method (and the system components) for implementing that method. The specific procedures applicants currently prefer are described herein as an exemplary way of carrying out applicant's invention, and from that description, the manner in which applicants disclosed system and method might be modified, and yet follow the principles of the present invention, will be apparent to those in the art.

It is initially important to note that applicants invention is primarily focused on enhancing a donor/recipient's immune system through autologous administration of that donor/recipient's stem cells collected when that donor/recipient is in a healthy condition, processed to provide the YoungBlood™ product, and administered preventively to that donor/recipient at a time, or under circumstances, when the donor/recipient is healthy but more at risk of developing diseases, as opposed to using the stem cells to therapeutically treat a specific disease that has already manifested itself in the donor/recipient. However, it should also be noted that applicant's method can also be used where the donor/recipient has manifested symptoms of a disease or condition for which autologous administration of the donor/recipient's stem cells can enhance the state of the donor/recipient's immune system as part of the treatment of that disease or condition.

According to the invention the immune system of a donor/recipient is enhanced by (a) collecting stem cells from the donor/recipient at a time that the donor/recipient appears to have a healthy immune system, taking into consideration the age of the donor/recipient and the characteristics of a healthy immune system for a donor/recipient of that age, (b) processing the stem cells (to form the YoungBlood™ product) and storing the stem cells (i.e. the YoungBlood™ product) in a condition that enables the stem cells to be later administered to that donor/recipient in predetermined amounts, in serial (consecutive) fashion, over predetermined time intervals, and (c) at the later request of the donor/recipient, administering the stem cells to the donor/recipient in serial (consecutive) fashion, over predetermined time intervals, to enhance the donor/recipient's immune system. By enhancing the donor/recipient's immune system in this manner, the donor/recipient's healthy life span can be increased.

As a further overview of the invention, autologous administration of a donor/recipient's stem cells (i.e. as the YoungBlood™ product), would be repeatedly done (i) at his/her late age (e.g. after 50-70 yrs. of age or during the last quarter of the donor/recipient's expected life span), or (ii) based on annual screening of the donor/recipient's immunological status and when indicated, an enhancement (booster) of his/her own stored bone marrow stem cells (BMSC), i.e. the YoungBlood™ product, would be designed to improve the donor/recipient's immunological status. The booster would comprise serial (consecutive) administrations of peripheral blood stem cells (the YoungBlood™ product), derived in the youth of the same individual by apheresis procedure.

One component of applicant's method is collecting stem cells from the donor/recipient when the donor/recipient appears to have a healthy immune system (i.e. preferably in his/her youth). Collection of the stem cells from the donor/recipient is performed at a time that the donor/recipient appears to be healthy, i.e. to have a healthy immune system, taking into consideration the age of the donor/recipient and the characteristics of a healthy immune system for a donor/recipient of that age. Such conditions coincide with the average healthy condition of a blood donor or of a bone marrow donor. The collectors will respect good practices for autologous HSC collection as given in Standards for Cellular Therapy Services, 6th Ed., of the American Association of Blood Banks and in FACT-JACIE International Standards For Cellular Therapy Product Collection, Processing, and Administration, Fifth Edition, 2012, and in Europe by the Guide to the Safety and Quality Assurance for the Transplantation of Organs, Tissues and Cells, 4th Edition, European Directorate for the Quality of Medicines & HealthCare, as well as future updates of these international recommendations and regulations. These regulations deal with all necessary physical characteristics that warrant good health of the donor, thereby preventing any risk of detrimental effects of the autologous BM HSC donation by apheresis, apart from the normal rate of possible side effects.

Mobilization of peripheral HSCs is important, in the implementation of applicant's invention. Normally, peripheral blood contains very few stem cells. Thus, in the applicant's method, in providing the YoungBlood™ product, the human stem cells (HSC) have to be mobilized, to provide an increased peripheral blood (PB) concentration of colony-forming cells. Currently, applicants prefer administration of G-CSF to the donor/recipient to produce mobilization of the stem cells to provide adequate collection of the stem cells for storage and later autologous cell administration to that donor/recipient. This can be updated by future state-of-the-art recommendations and best practices of aforementioned regulations.

Applicant's method presently contemplates obtaining a minimum number of CD34/kg ($\geq 2 \times 10(6)$/kg) stem cells, for autologous stem cell administration, Applicants describe below three (3) versions of a collection schema for storage and autologous administration, according to the present invention. This is based on studies that have shown that for autologous stem cell administration, an optimal CD34+ cell dose which leads to rapid and sustained recovery is thought to be between $2-5 \times 10(6)$/kg (Gorin et al. 2006; Baron et al. 2005; Pulsipher et al. 2009). On the other hand, $\geq 2 \times$/kg is accepted as the minimum threshold below which consistent and rapid multilineage engraftment, especially of platelets, may not take place. In an average size (e.g. 70 kg) individual, this means $\geq 140 \times 10(6)$ CD34+cells.

Collection of HSCs from mobilized peripheral blood (PB) is performed by mobilizing hematopoietic stem cells into the peripheral blood by using granulocyte colony-stimulating factor (G-CSF), or its pharmaceutical alternatives that are known to those in the art, and collecting the cells by continuous large volume (15-25 L) apheresis. The apheresis procedure can be repeated 2-3 times.

If some individuals fail to mobilize an adequate number of stem cells, Plerixafor (an inhibitor of the CXC chemokine receptor 4 CXCR4 on stem cells mediating adhesion) will be given to the donor/recipient to enhance mobilization of the stem cells. (Hauge et al. 2014; Keating 2011; Raffoux and Gluckman 1993; To et al. 2011).

Healthy individuals are usually fair mobilizers. However, a limited BM reserve indicated by a low platelet count prior to mobilization, low bone marrow cellularity, baseline low peripheral blood CD34+numbers, age and diabetes are risk factors for poor PBSC mobilization. Therefore in accordance with the present invention, the HSC collection is performed when the donor/recipient is in a healthy condition. Luckily for the donor/recipient, hematopoietic stem cells collected from poor and good mobilizers have been found to be qualitatively equivalent (Jiang et al. 2012).

Guidance regarding further medical assessment, the procedures used to agree requests, frequency and timing of donation and timing and duration of donor follow up is provided by the WMDA working group (Confer et al. 2011), and is regularly updated.

The foregoing discussion of the collection of HSC's takes into consideration the importance of homing of young autologous bone marrow cells into the bone marrow of aged recipient, their displacement capacity, and the resulting chimerism (i.e. the percentage of old cells that will be displaced by the administered cells).

Applicants have determined that in humans, injection of one whole average unit of mobilized HSCs (approx. $280 \times 10(6)$ HSCs) would lead to complete chimerism, (i.e. theoretically this number would allow a displacement of approx. 179% of host cells, if this was a linear function), i.e. displacement of all host cells in the bone marrow. However, this is in practice impossible due to non-linear homing capacity of grafted cells. If aliquoted to 5 times $56 \times 10(6)$ cells (which is currently one of applicants preferred collection schemas), one injected dose of $56 \times 10(6)$ cells would lead to approximately up to 36% chimerism, which applicants believe is immunologically satisfactory for an average size human (e.g. about 70 kg), see Table 1.

FIG. 2 shows the rate of homing/displacement of stem cells, based on animal experimentation from several authors. In FIG. 2, the highest rate of engraftment into host BM achieved in animal experiments was around 56%, which shows that displacement of host aged stem cells cannot be complete in non myeloablative setting.

Applicants have also determined that repetitive administration of a standard dose of BMC (i.e. the YoungBlood™ product) would contribute to a stronger and long lasting engraftment of blood-forming stem cells in the donor/recipient. Since an average PB HSC product contains $\sim 280 \times 10(6)$ HSCs, it could be aliquoted to 20 aliquots of $\sim 14 \times 10(6)$ HSCs, which could be theoretically used for a serial (consecutive) autologous administrations. One aliquot would be then theoretically capable of $\sim 9$% engraftment into BM (i.e. 9% displacement of old stem cells) of the 70 kg donor/recipient (see Table 1). This dose could be increased up to 4 times, in order to obtain a higher dose $\sim 64 \times 10(6)$ HSCs per one serial transplant. One average PB HSC product will therefore allow 5 serial transplants in 5 consecutive periods (e.g. years), resulting in up to about 36% chimerism—(a targeted chimerism), each time.

According to the present invention, the stem cells are processed and stored (as the YoungBlood™ product) in a condition that enables the stem cells to be later administered to the donor/recipient in predetermined amounts, in serial (consecutive) fashion, over predetermined consecutive time intervals. Currently, applicant prefers annual administrations, as discussed further in connection with applicant's exemplary collection and administration schemas.

Once the HSCs are collected, the product is taken to the laboratory for processing (to the YoungBlood™ product) and cryopreservation. According to the present invention, collected and processed stem cells are further cryopreserved, and stored (as the YoungBlood™ product) at a cryocenter, for later administration to the donor/recipient. The stem cells are available to be later administered to the donor/recipient in serial (consecutive) fashion, over predetermined time intervals, to boost (enhance) the donor/recipient's immune system. That reason for a donor/recipient requesting the administration can be, e.g. the donor/recipient reaching an age (e.g. 50-70 years or entering the last quarter of the donor/recipient's expected life span) that makes autologous administration of the donor/recipients stem cells appropriate, or the donor/recipient notices signs that make the donor/recipient want to boost (enhance) his/her immune system, or the donor/recipient, in consultation with his/her physician, determines that preventive (enhancement) of the donor/recipient's immune system would be beneficial for prevention of immune related disorders of old age, and may prolong the donor/recipient's healthy life span.

According to the present invention, the final apheresis product (sometimes referred to herein as the YoungBlood™ product) will be aliquoted into equal aliquots to enable several consecutive administrations. An average final product before freezing (approx. 280 mL) will contain close to $40 \times 10(9)$ total nucleated cells (TNCs), or $25 \times 10(9)$ (or 66.3%) mononuclear cells (MNCs). It will contain approx. $280 \times 10(6)$ hematopoietic stem cells (HSCs) on average. This amount of stem cells is designed to be enough to displace, as completely as possible, host HSCs in bone marrow and result in a medically acceptable level of chimerism. The volumes of final stem cell product (also referred to as YoungBlood™ product) can also be smaller and more concentrated, while keeping the cell count in each of those volumes substantially the same.

Applicant's method currently contemplates 3 versions (schemas) by which the stem cells can be aliquoted, for storage and later administration to the donor/recipient in serial (consecutive) fashion, as follows:
a. Version 1. Final product is divided into 5 aliquots, each containing approx. 56 mL of final product ("final product" is the product that is ultimately administered to the donor/recipient). Every aliquot contains on average $56 \times 10(6)$ CD34+cells, diluted in approx. $5 \times 10(9)$ TNCs. When a single one of the aliquots is administered, up to 36% chimerism can be expected in the bone marrow. One aliquot could be administered every 1-2 years.
b. Version 2. Final product is divided into 4 aliquots, each containing approx. 70 mL of final product. Every aliquot contains on average $70 \times 10(6)$ CD34+cells, diluted in approx. $6.2 \times 10(9)$ TNCs. When one single aliquot is administered, up to 45% chimerism can be expected in the bone marrow. One aliquot could be administered every 2-3 years.
c. Version 3. Final product is divided into 3 aliquots, each containing approx. 93 mL of final product. Every aliquot contains on average $93 \times 10(6)$ CD34+cells, diluted in approx. $7.5 \times 10(9)$ TNCs. When one or more of the aliquots is administered, up to 60% chimerism can be expected in the bone marrow. One aliquot could be administered every 3-5 years.

Where the volumes of the final stem cell products are smaller, the stem cell product can be divided into aliquots with smaller volume.

As described herein, according to the principles of the present invention, the administration of the stem cell product to the donor/recipient is intended to be performed at the request of the donor/recipient at certain times, or under certain circumstances during the donor/recipient's life span. For example, it can be performed when the donor/recipient determines he/she wants the administration to enhance the donor/recipient's immune system, when the donor/recipient recognizes conditions that suggest that his/her immune system could use enhancement. Moreover, it can be performed when the donor/recipient, after consultation with medical personnel, recognizes conditions that suggest impairment, or oncoming impairment of the donor/recipient's immune system. An underlying objective of the present invention is that administration of the donor/recipient's stem cells (as the YoungBlood™ product) could be useful to enhance the donor/recipient's immune system, at a time when such enhancement could extend the healthy life span of the donor/recipient. Circumstances and conditions that could motivate a donor/recipient to seek the administration are further described below.

For example, numerous studies have shown that the majority of age related diseases are caused by dysfunction of the immune system; see the review by Alonso-Fernandez 2011 (Alonso-Fernandez and De la Fuente 2011). Nowadays it is accepted that aging impairs both innate and adoptive immunity and that almost every component of the immune system is affected (De la Fuente et al. 2005; De la Fuente 2008; Ortega et al. 2000; Sebastian et al. 2005).

Thus, the impact of age on innate immunity is significant in whether a donor/recipient may seek the administration. Dysfunction in innate immunity results in a reduced ability to provide an immediate response to bacterial and viral pathogens as well as to integrate with the adaptive immune response. This is due to alterations in the activity of a variety of innate immune cell receptors and their downstream signaling pathways, as well as changes in the numbers and functional capacity of certain cells in the circulation. With age, an impaired NK-cell cytotoxic capacity and decreased production of cytokines and chemokines by activated NK cells have been observed (Linton and Dorshkind 2004; Solana et al. 2006).

There is decreased response of dendritic cells (DCs) associated with an impaired migration and impaired competence of DCs as antigen presenting cells (APCs). The antigen-presenting capacities of peripheral blood monocytes from aged human subjects are compromised and the activities of infection-response proteins, such as heat shock proteins, may also be altered (Njemini et al. 2005). There is a general decline in macrophage functions (Sebastian et al. 2005). Aging has been associated with alterations in the pro-inflammatory/anti-inflammatory cytokine release disbalance. Adherence capacity to tissues, expression of Toll-like receptors such as TLR2 or TLR4, or production of pro-inflammatory cytokines, are increased with aging (De la Fuente et al. 2004; De la Fuente et al. 2005; De la Fuente 2008; De la Fuente et al. 2008).

Aging neutrophils show greater adherence (Alonso-Fernandez et al. 2008; De la Fuente et al. 2005; De la Fuente et al. 2008; Lord et al. 2001). Also, alterations of membrane fluidity result in the reduction in downstream signaling events in old neutrophils (Fortin et al. 2007; Tortorella et al. 2007). Neutrophils from elderly subjects show a decreased chemotactic activity (De la Fuente et al. 2005; Lord et al.

2001; Niwa et al. 1989; Wenisch et al. 2000). The efficiency of migration to the infected site is affected as a result of reduced chemotactic ability, and associated with increased morbidity and mortality in aged patients with infections after trauma (Egger et al. 2004; Niwa et al. 1989). In addition, the phagocytic capacity of neutrophils decreases with age (Alonso-Fernandez et al. 2008; Butcher et al. 2001; Wenisch et al. 2000) and this will allow a greater development of infections. Also, the respiratory burst has been shown to be altered in neutrophils from aged volunteers; superoxide (O2-) and hydrogen peroxide (H2O2) production by neutrophils from aged humans is increased when compared to cells from the young (Alonso-Fernandez et al. 2008; Lord et al. 2001).

Moreover, the impact of age on adaptive immunity can be an important factor as to whether a donor/recipient seeks the administration.

Dysfunction of adaptive immunity results in a reduced ability to provide adaptive response to pathogens and in increased auto destructive tendencies of immune system. It is caused by impairment of B and T cell compartments.

In addition, impaired B-cell development and function is another factor that may affect whether the donor/recipient seeks the administration. The number of B lymphocytes is decreased in aged humans, and the B cell repertoire is decreased (Weksler 2000). With aging, decreased production of long-term immunoglobulin-producing B lymphocytes appears (Stephan et al. 1996), and progressive decline in the number and size of the germinal centers (GC) has been reported (Zheng et al. 1997). This results in a decreased antibody affinity maturation and antibody-secreting plasma cells in the bone marrow (Manz et al. 1997). Similarly, peripheral B cell percentages and numbers significantly decrease (Franceschi et al. 1995; Frasca et al. 2008; Shi et al. 2005). Both naïve and memory B cells show defects in class switch recombination (CSR) (Frasca et al. 2008). Therefore memory cells are deficient in number and function (for CSR) (Frasca and Blomberg 2009). Besides, shrinkage in receptor repertoire, increased amount of autoantibodies, and reduced response to vaccination are reported (Listi et al. 2006; Weksler and Szabo 2000; Weksler 2000). Differences in B cell homing and recirculation processes with age may occur and also have been shown as defects in Peyer's patch B cell function (Banerjee et al. 2002). Intrinsic changes in B cells also occur and have a significant impact on antibody production (Frasca and Blomberg 2009).

Impaired T-cell development and T cell function emerges with age (Miller 1996). Defects in the early T lineage precursor population, in recent thymic emigrants and in the homeostatic control of memory and naïve T cell populations have been revealed in the elderly. Aging is associated with involution of the thymus leading to a reduction in its contribution to the naïve T cell pool (Lazuardi et al. 2005). With aging the peripheral T lymphocyte populations show a shift from naïve to memory phenotype cells (Lazuardi et al. 2005). This results in decreased responsiveness to new antigens followed by reduced responses to vaccination (Frasca et al. 2007; Weinberger et al. 2008) and attenuated delayed-type hypersensitivity (DTH). There is an increase in the number of activated/memory T cells that causes an accumulation of cells that fail to respond to stimuli as efficiently as T cells from younger individuals (Baumgartner et al. 1980; Naylor et al. 2005). Naïve lymphocytes with aging loose the diversity of the antigen-recognition repertoire (Goronzy et al. 1998), and their production gradually declines (Franceschi and Cossarizza 1995; Goronzy et al. 1998). Non-stimulated proliferative response is diminished in aged subjects, whereas the proliferative response and interleukin-2 (IL-2) production significantly decline (De la Fuente et al. 2008). Lymphocyte functions undergo several other important age-associated alterations with aging, such as greater adherence to endothelium, lower chemotaxis capacity, decreased proliferative response to mitogenic stimulation and altered cytokine production (Arranz et al. 2008; De la Fuente 2008), leading to inflammation and vascular aging or vascular diseases (Yu and Chung 2001). In addition, the adaptive arm of the immune system has been suggested as an important factor in brain function. The cytokine milieu at the choroid plexus (CP) epithelium is affected by peripheral immunosenescence, with detrimental consequences to the aged brain. Amenable to immunomodulation, this interface is a unique target for arresting age-related cognitive decline (Baruch et al. 2013).

All these data suggest that a complex remodeling of adaptive immunity is characteristic of immunosenescence. New therapies should lead to new avenues for stimulating the output of naïve cells thus maintaining a healthy memory-lymphocyte pool (Alonso-Fernandez and De la Fuente 2011). Administration of one's own young pool of fully immune competent hematopoietic stem cells obviously seems to cover this possibility.

In determining whether a donor/recipient would seek the administration, it is also helpful to discuss criteria for establishing the impairment of the immune system, such that autologous administration of the donor/recipient's stored stem cells, according to the principles of the present invention could be beneficial to the donor/recipient (i.e. when should the donor/recipient receive an enhancement—booster—of immune system).

An underlying premise of the present invention is that it provides for preventive boosting/rejuvenating/enhancement of the immune system by administering the cells to the donor/recipient, before any signs of disease appear. By this preventive process, young HSCs can be administered to the donor/recipient at a time in his/her expected life cycle (e.g. in fourth quarter of the expected life span, when the donor is in the 50-70 year age, or at an age that responds to his/her familial health history (e.g. according to anamnestic data on his/her parents' health in old age), where enhancement of the immune system could be expected to be particularly beneficial.

In addition, the administration can take place when the donor/recipient shows signs that would predict an oncoming compromise of the donor/recipient's immune system. For example, the immune system of an aged donor/recipient can be monitored regularly (e.g. in the age range of 50-70, but also earlier), and administration of the stored stem cells to the donor/recipient can be used in cases any immune disbalance are recognized. This approach needs a close supervision and cooperation of an experienced immunologist and the aged donor/recipient's medical doctor. Various immune monitoring standard assays can be used for measuring and assessment of immunity status. Several standardized approaches are available, based on standardized immunoassays for measuring immune parameters, cancer markers, and multiple cytokines simultaneously, using either Luminex (up to 63 analytes) or MesoScale Discovery (MSD, up to 10 analytes) systems, other soluble proteins on the MSD platform (see http://www.mesoscale.com); mass cytometric tests, gene expression and miRNA microarrays, and microfluidic qPCR arrays for immune markers analysis, flow cytometry based immunophenotyping, phosphoepitopes, intracellular cytokine assays, immunity related total proteome, transcriptome and metabolome screening, etc. It is expected, that high throughput immune screening will develop substantially during next few years, allowing a huge improvement of donor/recipient personalized medicine. (See the Stanford School of Medicine, Institute for Immunity Administration and Infection, Human Immune Monitoring Center (HIMC) http://iti.stanford.edu/himc/).

Also, sexual functions (i.e. impairment or fading of reproductive capacity and sexual functions, as would be understood by those in the art), reflect the aging process and can be a predictor of compromise of the immune system. According to the so-called "disposable soma theory of aging", the somatic organism is effectively maintained only for reproductive success; afterwards it is disposable. Therefore, the somatic maintenance (in other words longevity) has a cost. Life span is determined by equilibrium between resources invested in longevity versus those for reproductive fitness (Loison et al. 1999). Transferring this into human physiology would lead to conclusion, that once the reproductive cycle is over in humans, the aging process abundantly takes place. In men, the reproductive cycle slowly stops after age of 60, whereas in women this process takes place earlier (ovulation usually stops after age of 50). Reproductive capacity and sexual activity slowly fades after the 60 years of age, however, there are huge individual differences, and so neither the sexual functions nor activities would be advisable as a sole criterion for the start of immune enhancement by administration of the donor/recipient's stem cells, according to the present invention.

Other individual physical signs of aging can also be taken into account, which depend on several factors, including genetics, such as skin changes (less elastic, wrinkles, dry skin), thinning of hair, greying of hair, loss of height, loss of hearing and decline in vision, especially night vision, changes in sleep, osteoporosis, loss of musculature, slowing of the metabolism, etc.

An exemplary implementation of the applicant's process is shown schematically in FIGS. 1a and 1b and in Exhibit A. FIGS. 1a and 1b and Exhbit A show the system components and their relation to each other for carrying out the method of the present invention. In those figures and Exhibit A, reference to ICT is intended to refer to the applicant's central processing system (e.g. a server or servers). It will also be apparent that applicant's method, as implemented by the system of FIGS. 1a and 1b and Exhibit A, has attributes similar to a one click system, in the sense that it is intended to collect and store relevant data, and once the donor/recipient want to participate in applicant's process establish contacts with donor/recipient (referred to as the "client"), the apheresis center, the cryocenter, a clinical translational center (for delivering the stored cells for administration to a donor/recipient) and establish scheduling, co-ordination of activities and generation of relevant data to enable the donor/recipient to gain the benefit of the process and the YoungBlood™ product.

A central processing system (the ICT data center) is selectively placed in circuit communication with the donor/recipient, e.g. via a website, to collect relevant data from the donor/recipient. In this application, "circuit communication" means communication by wire, cable, wireless, satellite, or any other accepted means of communicating establishing communications between devices. The central processing system is also placed in circuit communication with an apheresis center for collecting the stem cells, and in circuit communication with a processing and cell storing center (referred to as a cryocenter) for administering the storing of the cells and delivering the stem cell product for administration to the donor/recipient at a later stage of the donor/recipient's life cycle. The central processing system is selectively placed in circuit communication with the donor/recipient via a website, wherein relevant data is collected from the donor/recipient, the relevant data including donor/recipient data including administrative, financial, health related data; all of which enables a client file for the donor/recipient to be created for access by the central processing system. All data collected from the donor/recipient is stored in the client file which is accessible by the central processing system and all relevant data collected from the donor/recipient that relates to the collection, storage and administration of the donor/recipient's stem cells is transmitted to one or more apheresis centers and cryocenter (according to the donor/recipient's wishes in timing and proximity). An informed consent form is generated by the central processing system, using the health related data from the donor/recipient, and sent either to the donor/recipient, or to the apheresis center for initial review by appropriate medical personnel before being sent to the donor/recipient, and the informed consent form is then sent to the donor/recipient for execution by the donor/recipient. Once the donor/recipient has executed the informed consent form, the remainder of the process can be initiated, wherein an appointment between the donor/recipient and apheresis center is then made, and the cryocenter is informed about the forthcoming medical procedure (stem cell collection at apheresis center with subsequent transport of stem cells to the cryocenter for long-term storage), and relevant operational data (client's demographic and medical data relating to the specific collection and storage process, respectively) is provided to the apheresis center and the cryocenter.

Thus, the applicant's process links the key elements of the process (individual/client; apheresis/collection center; storage center/cryocenter) together and organizes the necessary elements of medical information, regulatory requirements (informed consent), administrative and logistical data, enabling payment, collection, storage, transport, contact and information exchange with the clinical translational center, and ultimate administration of the bone marrow cells (i.e. the YoungBlood™ product). Most, and preferably all, of the foregoing information can be delivered to the donor/recipient, so that the donor/recipient at all times has this information in his/her possession.

As seen from the foregoing detailed description, applicant has provided a new and useful process that provides collection of a donor/recipient's stem cells when the donor/recipient is in a healthy state, and autologous administration of a donor/recipient's stem cells (in the form of the YoungBlood™ product) to that donor/recipient at a later time, or under circumstances, where that administration can enhance the immune system of the donor/recipient, and potentially increase the healthy life span of the donor/recipient. FIG. 3 schematically illustrates the applicant's expectation of the manner in which an extension of a donor/recipient's healthy life span might result from the practice of the present invention. The life expectancy at birth of US citizen in 2012 was 79 years (76 for men and 81 for women), whereas the healthy life expectancy at birth (HALE)—i.e. the average number of years that a person can expect to live "full heath")—was 70 years. Therefore, the optimal age for starting prevention with the YoungBlood™ immune enhancement product is before 70 years of age, (e.g. between 50-70 years of age), if the person is generally healthy. This will increase the period of fully health at least until 80 years of age, postpone the appearance of disease and increase the life span accordingly.

Applicants provide the following additional information that will be helpful to those in the art in connection with the present invention.

1. Some Further Information and Data on Homing of Young Bone Marrow Cells into the Bone Marrow of Aged Recipient, Displacement Capacity, and the Resulting Chimerism.

In order to achieve successful engraftment of the stem cells in BMT, two conditions must be met: a) the stem cells must be effectively nested in their niches (the so-called "homing"), and b) these stem cells must successfully proliferate and differentiate into hematopoietic and immune tissue. Applicants expect that the young stem cells will effectively engraft in the bone marrow of the recipients, and that these cells will retain the ability of the proliferation and differentiation.

There is very little or no data on displacement of old HSCs by young HSCs in autologous settings in healthy humans. Thus, it is necessary to rely on data obtained in irradiated or conditioned patients, or on animal studies. Luckily, although animal studies are generally not capable to be transferred to the human biology, this is not the case in bone marrow transplantation. Data and findings regarding murine bone marrow transplantation, based on the biology of stem cells, has been in history transferred into human therapy with high fidelity, which was not the case with some other pharmaceutical agents. As a result, results from mice studies were always good enough to allow the development of bone marrow transplantation in humans, based on deduction from the animal studies.

In humans, data were mostly obtained from patients. Recommendations for allogeneic transplantation differ from those for autologous transplantation. In the allogeneic transplantation settings, the HSC niche is usually conditioned by irradiation or chemotherapy, which is not the case in some autologous settings.

2. Various authors have shown that grafting of HSCs into nonmyeloablated (non-irradiated or chemotherapy treated) mice is feasible, and results in stable long term engraftment (Till and McCulloch 1961a; Micklem et al. 1968; Brecher et al. 1979; Brecher et al. 1982); (Nilsson et al. 1999); (Saxe et al. 1984); (Stewart et al. 1993a; Stewart et al. 1993b;) Wu and Keating 1993); Ramshaw et al. 1995b). (Domen et al. 2006);

3. Calculation—Deductions from Human and Mice Studies

An adult female BALB-c mouse weights on average 20 g and possesses approx. 500-600×10(6) bone marrow cells (Kovina et al. 2013; Colvin et al. 2004). Based on simple comparison, a 70 kg human adult has around 1.7×10(12) bone marrow cells. If more elaborated data of Bianconi 2013 is used, the total human cell number is 3.72×10(13) and the bone marrow consisting of 4% of the total body mass contains approx. 1.5×10(12) cells (Bianconi et al. 2013).

According to Colvin (2004), total bone marrow cellularity in BALB/c mice is 530±20 million cells; stable from 8 weeks to 1 year of age. C57BL/6J mice had 466±48 million marrow cells. Using these data, theoretical models of infused marrow (40 million cells) replacing or adding to host bone marrow give chimerism values of 7.5% and 7.0%, respectively; the observed 8-week engraftment of 40 million male BALB/c marrow cells into female hosts (72 mice) gave a value of 6.9% (Colvin et al. 2004). Similar experiments of the applicant resulted in 13% chimerism after injection of 63 million cells, measured between 6 and 12 weeks after transplantation, which confirms the data from literature specified above.

Additional evidence for support of this hypothesis comes from experiments performed by Ramshaw et al, in which varying doses and schedules of male BALB/c marrow were infused into non-treated female BALB/c hosts showing that engraftment was 0.17% per million BM cells infused. Therefore if 40×10(6) cells were infused, the resulting chimerism would be 6.8%. This same report indicated that neither marrow cellularity nor content of progenitors was increased in mice injected with 200 million marrow cells over 5 days (Ramshaw et al. 1995a). In further work Blomberg et al injected a total of 800 million marrow cells over time into nonmyeloablated BALB/c mice and showed that there was no increase in marrow or splenic cellularity (Blomberg et al. 1998). In present experiments, the highest degree of obtained chimerism after BMT was on average 50%, with rather high individual deviation ±30%.

If the formulas of Rao and Colvin are taken into account, transplantation of 1 million bone marrow cells containing approximately 100 hematopoietic stem cells results in 0.17% to 0.28% of chimerism in mice (Colvin et al. 2004; Rao et al. 1997). In the study of the applicant, transplantation of 1 million BM cells led to 0.21% chimerism on average, which confirms the data from the literature. Consequently, the following numbers of BM cells (i.e. TNCs—total nucleated cells of the bone marrow) are needed for achieving measurable chimerism, as detailed in Attached Table 1:

Table 1 and FIG. 2 show the chimerism after linear displacement of BM stem cells from their niches, when healthy BM cells are transplanted and homed. It is noted that the calculated dosages actually correspond to the current clinical practice of autologous transplantation. Namely, if the lowest dose is >2×10(6) HSCs per 1 kg, one 70 kg individual should receive >140×10(6) HSCs for successful and complete engraftment. In fact, this number theoretically results in 94% of chimerism in the case the recipient is not conditioned by immune depletion (irradiation or chemotherapy). In practice, higher numbers of HSCs are transplanted with the donated HSC units from healthy donors, at least 280×10(6) HSCs or more. In some Apheresis collection centers, the average HSC units contains up to 350×10(6) HSCs. If linear homing would result, this figures would lead to displacement (chimerism) of up to 179% of host BM stem cells (see Table 1). However, the dynamics of displacement and homing is in practice not linear but skewed, since even the transplantation of large numbers of BMCs (i.e. 150% of total BMC number) into non-immunoablated host never reaches a 100% displacement, but only approx. 56% on average. See FIG. 2.

FIG. 2 shows Non-linear (skewed) engraftment of BMCs in mice. The highest rate of engraftment into host BM achieved in animal experiments was around 56%, which shows that displacement of host aged stem cells can not be complete in non-myeloablative setting.

One average mobilized HSC unit from a healthy bone marrow donor has around 200 mL volume and contains approx. 40×10(9) total nucleated cells (TNCs), within this there are approx. 25×10(9) mononuclear cells (MNCs), which contain a subpopulation of approx. 280×10(6) HSCs. (Table 2 attached). Table 2 shows average figures of 1 mobilized product of HSC (26 apheresis procedures, healthy donors, collected in BTC Ljubljana 2012-13)

Based on the data of Tables 1 and 2, and FIG. 2, applicants have determined that in human, injection of one whole average unit of mobilized HSCs (approx. 279×10(6) HSCs) would lead to complete chimerism (approx. 179% chimerism if this was a linear function), i.e. to displacement of all host bone marrow HSCs. As mentioned, this is not possible in practice due to non-linear homing capacity of grafted cells in the host cell environment. If aliquoted to 5 times 56×10(6) hematopoietic stem cells, one injected aliquot dose of 56×10 (6) hematopoietic stem cells would lead to approx. 36% chimerism, which is probably immunologically satisfactory to enhance the aging stem cell environment in the bone marrow.

In the present invention, the donor/recipient is not immunodeprived, therefore the transplantation of young autologous HSCs will not cause a complete recovery by transplanted HSCs, but only a partial displacement of the old population of bone marrow residing stem cells, which will be replaced by the stored HSCs, leading to old/young cell chimerism. The proportion of the chimerism is dependent on the amount of cells transplanted, which takes place in a skewed-linear way. Our determinations are based on previous studies that have shown that stem cells engraft effectively or even better in the non-irradiated and non-conditioned recipients and that they establish a stable long-term multilineage hematopoiesis (Rao et al. 1997). This is probably due to the fact that host HSC microenvironment is injured by irradiation or chemical myeloablation (Plett et al. 2002).

On the basis of other publications and applicants' experience we have further determined that the repetitive transplantation of a standard dose of BMC would contribute to a stronger and long lasting engraftment of blood-forming stem cells in the recipient mice. Quesenberry et al. transplanted 40 million BM cells (containing approx. 4.000 long term HSCs) to non-irradiated mice recipients and achieved a 10% engraftment (Quesenberry et al. 1997; Quesenberry et al. 1994). Rao et al. 1997 have injected male BMC to the female recipients 1, 2, 3, 4 or 5 days in a row (each time 40 million BM cells), and discovered that the percentage of the engraftment into BM after 20-25 weeks (corresponding to approx. 20 years of human life span) increased with regard to the number of injections (11%, 20%, 23%, 32%, and 39%, respectively) (Rao et al. 1997). Blomberg et al. 1998 injected non-irradiated female mice recipients 20-times with 40×10(6) male BMC (i.e. approx. 3 times a week, altogether 800 million BMCs), and reached a high proportion of implantation (41% in the BM, 69% in the spleen, and 39% in the thymus), which was significantly higher than after a single application of 2×10(6) BMC, where the proportion of engrafted cells was much smaller (4%, 6% and 4%) (Blomberg et al. 1998). Colvin et al. in 2004 achieved a 30-37% chimerism after transplantation of 200×10(6) BM cells (Colvin et al. 2004). Similarly, applicants achieved an average 13% chimerism in the bone marrow with three serial infusions of 20×10(6) BM cells (accompanied by 1% chimerism in the lungs and 3.1% chimerism in the spleen). This confirms the concept of serial transplantation to be feasible.

4. The Relevance of Mouse Data in Confirming the Validity of the Present Invention.

Similarity of Mouse Data as Predictor of Human Results

Certain pharmacology studies that test therapeutic effect of chemical substances cannot be translated into human medicine. In contrast to those studies, animal studies on the biology of bone marrow and hematopoietic stem cell transplantation can be translated with certain degree of reliability. Namely, there is ample evidence in medical literature witnessing the feasibility of bone marrow biology and immunology to be deducted from mice and other animals to humans, and this close resemblance of the immune system allowed revolutionary procedures for curing cancer and other diseases, starting with Dr. E. Donnall Thomas's pioneering work in bone marrow transplantation, which led to him receiving the 1990 Nobel Prize in physiology or medicine, to the "fathers" of Stem Cell Science J. Till and E. McCulloch, who actually cemented the stem cell theory by publishing the results in the journal Nature in 1963 (Becker et al. 1963; Till and McCulloch 1961b). They and other researchers showed that the murine models function perfectly in these settings.

There are also studies of animal data that, while not directed to the present invention, provide results that confirm the underlying principles of applicants' invention.

There exist several animal studies that have proven the extension of life span by using stem cells. Lavasani et al. in 2012 showed that intraperitoneal administration of muscle derived stem cells (MDSC), isolated from young mice, to progeroid mice conferred a significant (up to ⅓) healthy lifespan extension. They used low numbers of MDSCs, mice were injected intraperitoneally with 2-4×10(5) young MDSPCs per gram body weight. The transplanted cells also improved degenerative changes and vascularization in tissues where donor cells are not detected, suggesting that their therapeutic effect may be mediated by secreted factor(s) (Lavasani et al. 2012).

Similarly, Shen et al. (2011) observed that transplanting mesenchymal stem cells (irradiated mice, 1×10(6) BMSCs transplanted) from young to old mice significantly slows the loss of bone density and, and surprisingly, prolongs the life span of old mice, who lived 890 days compared to 765 days of the control mice (Shen et al. 2011).

A similar study of Kovina et al. in 2013 showed that the average lifespan of non-myeloablated old mice with 21.5 months can be extended by transplantation of young bone marrow cells, and the life span in treated group was 1.4 months longer than in non-treated controls (26.5 vs. 25.1 months, respectively). This would result in 39% increase of life span after the transplantation. They transplanted up to 1.5×10(8) BM cells, that is, about 25% of the total BM cells of the mouse (Kovina et al. 2013).

Stem cell aging can be slowed by exposure to humoral factors from a young parabiont (sharing circulation with an old mouse) (Villeda et al. 2011; Conboy et al. 2005). Besides, implantation of young stem cell environment into aged animal can even induce the enhancement of existing, old regenerative capacities. When exposed to youthful influences, aged stem cells adopt a more youthful potential and such tissue regeneration phenotype was due to the resident stem cells (Conboy et al. 2013).

5. Length of Storage

Cryopreserved human hematopoietic stem cells can be stored for very long periods. Cryosaved cells retain engraftment potential after extended cryo storage (Spurr et al. 2002). The maximum time of frozen cells has not yet been determined. In 1987, The Office of Biologies Research and Review (OBRR) has approved storage of Red Blood Cells, Frozen for a maximum of ten years when prepared by certain methods. This extension of dating applies to red blood cells prepared with high glycerol methods (40% glycerol) and stored at −65 degree Celsius or lower.

Red blood cells as a blood bank product alone may be stored for ten years if the above requirements are met and appropriate testing for anti-HIV has been performed. No one knows what the maximum storage period might be. The current science of cryobiology tells us that cells which are cryogenically preserved remain viable for decades. For stem cells, storage period is thought to be up to 50 or even 100 years. It has been confirmed that cord blood stem cells were still viable after being frozen 23+ years. Thus, appropriately stored stem cells and other cells should be able to be stored indefinitely (Mazur 1970; Nietfeld 2008; Broxmeyer 2010).

Procedures for human embryo freezing were developed in 1984 and only went into widespread use in the late 1980s. This means that the longest time a human embryo has been stored is 25-30 years and, typically, patients that have left embryos in storage for this long are not coming back for them. Some patients have come back after 10-12 years and the embryos have been thawed successfully and created healthy babies. Beyond this time frame, we don't know how long an embryo will remain viable, but it is possible that, kept in liquid nitrogen, an embryo may be viable indefinitely.

6. Further Information on when a Donor/Recipient should Benefit from Autologous Administration of his/her Stored Stem Cells, According to the Present Invention.

According to the WHO, the life expectancy at birth of a US citizen in 2012 was 79 years (76 for men and 81 for women), life expectancy at age 60 was 23 years (21 years men and 24 years for women), whereas the Healthy life expectancy at birth (HALE)—representing the average number of years that a person can expect to live in "full health"—was 70 years (68 years for men and 71 for women). Of course, in future further extension of human life span is expected at certain rate, which should be taken into account when planning the preventive immune enhancement by the YoungBlood™ product, according to the present invention. One forecasting model projects life expectancy in the United States to rise to 86 by 2075 and to 88 by the end of the century (Sonnega 2006).

Based on these data, it would be nowadays advisable to start the preventive course of YoungBlood™ immune enhancement product, according to the present invention, in the last quarter of the average life span. The optimal age for starting prevention with the YoungBlood™ immune enhancement product is around 70 years of age (and more preferably in the range of 50-70 years), if the person is generally healthy. The preventive serial administration of YoungBlood™ product will increase the period of full health to at least 80 years of age (now 70 years on average in US), further postpone the appearance of disease for an equal period of 10 years or more, and increase the life span accordingly. See FIG. 3.

7. Expected Extension of Life Span

FIG. 3 shows the expected extension of a healthy life span by using the YoungBlood™ immune enhancement product. The life expectancy at birth of a US citizen in 2012 was 79 years (76 for men and 81 for women), whereas the healthy life expectancy at birth (HALE)—i.e. the average number of years that a person can expect to live in "full health"—was 70 years. Therefore the optimal age for starting prevention with the YoungBlood"" immune enhancement product is around 70 years of age, if the person is generally healthy. This will increase the period of full health at least until 80 years of age, postpone the occurrence of disease and increase the life span accordingly.

8. Additional Beneficial Effects that May be Expected from the Practice of the Present Invention The YoungBlood™ product delivers a booster to the stem cell population, enhancing the general stem cell capacity It seems that young stem cells improve various organs. Recent studies of Wagers et al. in parabiotic mice confirmed that heterochronic parabiosis reverses age-related cardiac hypertrophy. They identified a protein called GDF11, a circulating member of TGF-(3 family, that declines with age and that reverses age-related cardiac hypertrophy, i.e. rejuvenates hearts of old mice. Increased GDF11 levels in aged mice also improved muscle structural and functional features and increased strength and endurance exercise capacity. These data indicate that GDF11 systemically regulates muscle aging and may be therapeutically useful for reversing age-related skeletal muscle and stem cell dysfunction (Loffredo et al. 2013).

A recent article of Holstege et al. (Holstege et al. 2014) documented the evidence of aging of stem cells in the somatic mutations study of a 115 years old female and showed that the mutations were ample, but uneventful, whereas on the other side, her stem cells were close to the point of exhaustion. Namely, majority of her peripheral white blood cells were offspring of only two hematopoietic stem cell (HSC) clones that survived to her old age, implying that most or all of the blood stem cells she started life with had already burned out and died. The telomere lengths of her immune cells, i.e. leukocytes, were significantly shorter than telomere lengths from other tissues. On average, the telomeres on the white blood cells were 17 times shorter than those on brain cells, which hardly replicate at all throughout life. Together, this suggests that the finite lifespan of HSCs leads to hematopoietic and immune exhaustion at old ages. What they found suggests that our lifespan might ultimately be limited by the capacity for stem cells to keep replenishing tissues. Once the stem cells reach a state of exhaustion that imposes a limit on their own lifespan, they themselves gradually die out and steadily diminish the body's capacity to keep regenerating vital tissues and cells, such as immune system.

Finally, in the population of BM derived HSCs there exist a small population of very primitive progenitors, named VSEL (very small embryonic like stem cells), that are kept quiescent in adult tissues and exhibit some characteristics of long-term repopulating hematopoietic stem cells (LT-HSCs), and may differentiate into organ-specific cells. What is amazing is the fact that the number of these cells positively correlates in several murine models with longevity, and that these cells can be found together with HSCs in the bone marrow, mobilized peripheral blood, and umbilical cord blood, proving the concept of YoungBlood™ system for extending the life span in humans (Ratajczak et al. 2008; Zuba-Surma et al. 2009; Ratajczak et al. 2012).

In addition, young stem cells work favorably on brain and enhance cognitive capabilities. Thus, in addition to enhancing the immune system, the YoungBlood™ product can also enhance the cognitive function of the donor/recipient.

In the central nervous system (CNS), aging results in decline in neural stem/progenitor cells and neurogenesis, with concomitant impairments in cognitive functions (van Praag H. et al. 2005). In 2011 Villeda first reported that exposing a young animal to plasma from old mice decreased synaptic plasticity and impaired contextual fear conditioning and spatial learning and memory. Increasing peripheral CCL11 chemokine levels in vivo in young mice decreased adult neurogenesis and impaired learning and memory. Together their data indicate that the decline in neurogenesis, and cognitive impairments, observed during aging can be attributed to changes in blood-borne factors. Later on in 2014, the group of Villeda found that the neurons in the hippocampus of the old mice after parabiosis sprouted new connections. An 18-month-old mouse that is considered to be equivalent in age to a 72-year-old person, was joined with one to two month old mice. Parabiosis caused that dendritic spine density of mature neurons increased and synaptic plasticity improved in the hippocampus of old mice. Similarly, if the plasma from the blood of young mice was injected into old mice, it caused the old mice to perform far better on memory tests. This means that at the cognitive level, systemic administration of young blood plasma into aged mice improved age-related cognitive impairments in both contextual fear conditioning and spatial learning and memory (Villeda et al. 2014).

Similarly, Katsimpari et al. in 2014 reported that parabiosis spurred the growth of blood vessels in the brain. They showed that factors found in young blood induced vascular remodeling, culminating in increased neurogenesis and improved olfactory discrimination in aging mice. 3D reconstruction of the brain, and magnetic resonance imaging (MRI) of the mouse brain showed more new blood vessels and more blood flow, both of which are normally associated with younger, healthier brain tissue. Younger mice have a keen sense of olfactory discrimination, they can sense fine differences in odor, so they avoided the smell of mint; the old mice didn't. But the old mice exposed to the blood of the young mice, and those treated with GDF11, did. Further, they injected GDF11 alone into the mice and found that it spurred the growth of blood vessels and neurons in the brain, although the change was not as large as that from parabiosis. Obviously, the factors that slow the age-dependent deterioration of the neurogenic niche in mice may constitute the basis for new methods of treating age-related neurodegenerative and neurovascular diseases (Katsimpardi et al. 2014).

Interestingly, another animal model of heterochronic parabiosis (mice with shared circulation) demonstrated the capacity of young immune system in the regeneration of myelin sheaths, which are degenerated by old age. Ruckh et al. have recently showed that in the central nervous system (CNS), remyelination of experimentally induced demyelination is enhanced in old mice exposed to a youthful systemic milieu. Remyelination in old animals involved recruitment to the repairing lesions of blood-derived monocytes from the young parabiotic partner, and preventing this recruitment inhibited rejuvenation of remyelination. These data suggest that enhanced remyelinating activity requires both youthful monocytes and some other factors, and that remyelination-enhancing therapies targeting endogenous cells can be effective throughout life (Ruckh et al. 2012). This finding poses a significant promise to therapy of long-term demyelinating diseases such as multiple sclerosis (MS) by autologous transplantation of stored young immune tissues.

Finally, it is contemplated that the administration of the autologous stem cells to the donor/recipient may be performed when the donor/recipient's immune system is affected by disease (e.g. Crohn's disease) that results in unwanted clones of sick cells and therefore later immunomodulated by therapy in such a way that removes unwanted clones of sick cells, which consequently allows infusion of autologous stem cells to this donor/recipient in accordance with the present invention, to enhance that donor/recipient's immune system.

With the foregoing disclosure in mind, it is believed that various adaptations of applicant's process, which apply the principles of the present invention, will be apparent to those in the art.

The invention claimed is:

1. A method for enhancing the immune system of a client, comprising
 a. collecting autologous hematopoietic stem cells from a client before age-associated decline in immune system function in said client, wherein the collecting of cells occurs in a single collection;
 b. storing the autologous stem cells under storage conditions that enable maintenance of stem cell properties until later administration of said stem cells to said client, and
 c. administering said stored autologous stern cells to said client at one or more time points later in life when an age-associated decline in immune system function occurs in said client but prior to developing symptoms of a disease, which limits the life span of the client, wherein at least a portion of the administered autologous stern cells engraft in and repopulate the bone marrow with functional immune progenitor cells, thereby enhancing the immune system of said client.

2. The method of claim 1, comprising further collecting of relevant data of said client, selected from administrative, financial and/or health data, and storing said data in electronic form in a central information processing system that is placed in circuit communication, enabling transfer of relevant data in electronic form, with:
 i. a collection center that collects the autologous stem cells,
 ii. a cell storing center that stores the autologous stem cells, and
 iii. an administration center for administering the stored stem cells to said client later in life of said client.

3. The method of claim 1, wherein the administration of the stored autologous stern cells to the client is performed when the client presents symptoms of impairment of the immune system.

4. The method of claim 1, wherein the administration of the stored autologous stern cells is performed when the client shows age related impairment or fading reproductive capacity and/or sexual functions.

5. The method of claim 1, wherein administration of the stored autologous stem cells to the client is performed in the last quarter of the client's life expectancy.

6. The method of claim 1, wherein initial administration of the stored autologous stem cells to the client is performed when the client reaches 50-70 years of age.

7. The method of claim 1, wherein the collection of autologous stem cells from the client includes dividing the collected cells into a plurality of aliquots, each of which includes a sufficient number of autologous hematopoietic stem cells, as defined by CD34+ cell count or other appropriate marker for hematopoietic stem cells, such that when the aliquots are administered to the client, in serial fashion, a level of chimerism of the administered autologous stem cells and stem cells residing in the client at the time of administration occurs in the bone marrow of the client.

8. The method of claim 7, wherein the collected cells are present in a cell suspension that is divided into 5 aliquots, each containing approximately 56 mL of cell suspension, wherein every aliquot contains approximately $56 \times 10^6$ CD34+ cells, diluted in approximately $5 \times 10^9$ total nucleated cells (TNCs), and wherein when one or more of the aliquot is administered, the targeted chimerism occurs in the bone marrow of the client, and wherein one aliquot is administered about every 1-2 years.

9. The method of claim 7, wherein the collected cells are present in a cell suspension that is divided into 4 aliquots, each containing approximately 70 mL of cell suspension, wherein every aliquot contains approximately $70 \times 10^6$ CD 34+ cells, diluted in approximately $6.2 \times 10^9$ TNCs, and wherein when one or more of the aliquot is administered, the targeted chimerism occurs in the bone marrow of the client, and wherein one aliquot is administered about every 2-3 years.

10. The method of claim 7, wherein the collected cells are present in a cell suspension that is divided into 3 aliquots, each containing approximately 93 mL of cell suspension, wherein every aliquot contains approximately $93 \times 10^6$ CD34+ cells, diluted in approximately $7.5 \times 10^9$ TNCs, and wherein when one or more of the aliquot is administered, the targeted chimerism occurs in the bone marrow of the client, and wherein one aliquot is administered about every 3-5 years.

11. A method for enhancing of the immune system of a client, comprising
    a. providing stored autologous hematopoietic stem cells collected from the client when healthy, and before age-associated decline in immune system function in said client, wherein the collecting of cells occurred in a single collection; and
    b. administering said stored autologous stem cells to said client at one or more time pointy later in life when an age-associated decline in immune system function occurs in said client but prior to developing symptoms of a disease, which limits the life span of the client, wherein at least a portion of the administered autologous stem cells engraft in and repopulate the bone marrow with functional immune progenitor cells, thereby enhancing the immune system of said client.

12. The method of claim 11, wherein the administration of the stored autologous stem cells to the client is performed
    i. at a time in the fourth quarter of the expected life span of the client;
    ii. at a time when the client is 50-70 years of age;
    iii. at an age of the client that corresponds to said client's familial health history, when enhancement of the immune system is expected to be beneficial;
    iv. at a time when monitoring of the immune function of the said client shows signs that predict a compromise of the immune system of said client; or
    v. at a time when the said client shows an impairment or fading reproductive capacity and/ or sexual functions.

13. The method of claim 1, wherein the administration of the stored autologous stem cells to the client is performed at an age that corresponds to the client's familial health history, when enhancement of the immune system is expected to be beneficial.

14. The method of claim 1, wherein the administration of the stored autologous stem cells to the client is performed when monitoring the immune function of the client shows signs that predict an oncoming compromise of the immune system of said client when enhancement of the immune system is expected to be beneficial.

15. The method of claim 7, wherein the collected autologous stem cells comprise a minimum number of CD34+ cells of $>2 \times 10^6$ cells/kg client body weight and are subsequently administered to the client in a plurality of aliquots.

16. The method of claim 15, wherein the collected autologous stem cells are aliquoted into 3 aliquots and subsequently administered every 3-5 years, or aliquoted into 4 aliquots and subsequently administered every 2-3 years, or aliquoted into 5aliquots and subsequently administered every 1-2 years.

* * * * *